(12) United States Patent
Noma

(10) Patent No.: US 12,130,247 B2
(45) Date of Patent: Oct. 29, 2024

(54) METHOD OF MEASURING PHYSICAL PROPERTIES, METHOD OF EVALUATING MEMBER, METHOD OF MANUFACTURING ELECTRONIC COMPONENT DEVICE, METHOD OF MANUFACTURING MATERIAL FOR ELECTRONIC COMPONENT DEVICE, AND PHYSICAL PROPERTY MEASUREMENT SYSTEM

(71) Applicant: SHOWA DENKO MATERIALS CO., LTD., Tokyo (JP)

(72) Inventor: Hirokazu Noma, Tokyo (JP)

(73) Assignee: RESONAC CORPORATION, Tokyo (JP)

( * ) Notice: Subject to any disclaimer, the term of this patent is extended or adjusted under 35 U.S.C. 154(b) by 0 days.

(21) Appl. No.: 17/926,998

(22) PCT Filed: Dec. 23, 2021

(86) PCT No.: PCT/JP2021/048024
§ 371 (c)(1),
(2) Date: Nov. 22, 2022

(87) PCT Pub. No.: WO2023/119594
PCT Pub. Date: Jun. 29, 2023

(65) Prior Publication Data
US 2023/0204530 A1 Jun. 29, 2023

(51) Int. Cl.
*G01N 25/16* (2006.01)
*G01N 5/02* (2006.01)
*G01N 25/58* (2006.01)

(52) U.S. Cl.
CPC ............... *G01N 25/16* (2013.01); *G01N 5/02* (2013.01); *G01N 25/58* (2013.01)

(58) Field of Classification Search
CPC ................................... G01N 25/16; G01N 5/02
See application file for complete search history.

(56) References Cited

U.S. PATENT DOCUMENTS

2022/0067904 A1* 3/2022 Frewein ............... G06V 10/751

FOREIGN PATENT DOCUMENTS

| JP | H03-245048 A | 10/1991 |
|----|--------------|---------|
| JP | 2015141152 A * | 8/2015 |

(Continued)

OTHER PUBLICATIONS

Takeshi Takatoya et al., "Deformation Behaviors of Unsymmetric CFRP Laminates with Moisture Absorption", Material System, vol. 20 (2002), p. 131-136.

(Continued)

*Primary Examiner* — Mirellys Jagan
(74) *Attorney, Agent, or Firm* — SOLARIS Intellectual Property Group, PLLC

(57) ABSTRACT

A method of measuring physical properties includes: a preparation step of preparing a moisened member containing an organic material and having a known water absorption rate and a known mass; a heating and cooling step of performing cooling after heating the member; and a measurement step of measuring a mass of the member after cooling the member in the heating and cooling step, in which in the heating and cooling step, a deformation rate of the member is measured using a digital image correlation method.

20 Claims, 3 Drawing Sheets

(56) References Cited

FOREIGN PATENT DOCUMENTS

JP 2018105670 A * 7/2018
WO 2012/161287 A1 11/2012

OTHER PUBLICATIONS

G Baschek et al., "Effect of water absorption in polymers at low and high temperatures," Polymer, vol. 40, Issue 12, pp. 3433-3441, 1999.
Yasumitsu Orii et al., "Material selection based on measurements of thermal deformation and mechanical properties by Digital Image Correlation," 2009 Proceedings of the National Conference of the Institute of Electrical Engineers of Japan, Mar. 19, 2009, S1513-1516.

* cited by examiner

METHOD OF MEASURING PHYSICAL PROPERTIES, METHOD OF EVALUATING MEMBER, METHOD OF MANUFACTURING ELECTRONIC COMPONENT DEVICE, METHOD OF MANUFACTURING MATERIAL FOR ELECTRONIC COMPONENT DEVICE, AND PHYSICAL PROPERTY MEASUREMENT SYSTEM

TECHNICAL FIELD

The present disclosure relates to a method of measuring physical properties, a method of evaluating a member, a method of manufacturing an electronic component device, a method of manufacturing a material for an electronic component device, and a physical property measurement system.

BACKGROUND ART

When an electronic material used for an electronic component or the like contains an organic material, properties thereof change due to moisture absorption. Therefore, changes in mechanical properties and electrical properties due to moisture absorption have been studied in electronic materials and electronic components including the same. For example, Non-Patent Document 1 (Takeshi Takatoya, James C. Seferis, "Deformation Behaviors of Unsymmetric CFRP Laminates with Moisture Absorption", Material System Vol. 20 (2002), p. 131-136) studies deformation of unsymmetric CFRP laminates due to moisture absorption in a state where the ambient temperature is controlled.

SUMMARY OF INVENTION

In the study on the deformation behavior of unsymmetric CFRP laminates due to moisture absorption disclosed in Non-Patent Document 1, it is assumed that the strain inside the laminate is an overlap of thermal strain caused by temperature change, strain caused by expansion due to moisture absorption, and the like, and these strains are independent of each other. That is, in Non-Patent Document 1, it is assumed that the deformation (thermal deformation) due to heat and the water absorption rate are independent of each other in the laminate.

However, depending on the type of organic material constituting the member such as the unsymmetric CFRP laminate, the thermal deformation and the water absorption rate in the member may not be independent. For example, there is a material or the like in which a thermal expansion coefficient when a member absorbs moisture is increased or decreased more than a thermal expansion coefficient of a dried member (Non-Patent Document 2; G Baschek et al., "Effect of water absorption in polymers at low and high temperatures," Polymer, Volume 40, Issue 12, Pages 3433-3441, 1999.). Therefore, in order to appropriately evaluate the relationship between the thermal deformation and the water absorption rate for a member containing an organic material, there is a need for a method of measuring physical properties by which the relationship between the deformation rate and the water absorption rate of the member can be evaluated for both a material in which the thermal deformation and the water absorption rate are independent and a material in which the thermal deformation and the water absorption rate are correlated.

The disclosure has been made in view of the above circumstances, and an object of the disclosure is to provide a method of measuring physical properties and a physical property measurement system capable of evaluating the relationship between the deformation rate and the water absorption rate of a member containing an organic material regardless of the correlation between the thermal deformation and the water absorption rate, and a method of evaluating a member, a method of manufacturing an electronic component device, and a method of manufacturing a material for an electronic component device including this method.

Solution to Problem

Specific means to solve the above-described problems are as follows.
<1> A method of measuring physical properties, the method comprising:
  a preparation step of a moistened member containing an organic material and having a known water absorption rate and a known mass;
  a heating and cooling step of performing heating and then cooling the member; and
  a measurement step of measuring a mass of the member at least one of during the heating and cooling step and after the heating and cooling step, and measuring a deformation rate of the member using a digital image correlation method.
<2> The method of measuring physical properties according to <1>, wherein, in the heating and cooling step, the member is heated and cooled within a range of −65° C. to 300° C.
<3> The method of measuring physical properties according to <1> or <2>, wherein the member is a measurement sample obtained from a multilayer wiring board, a laminate, a semiconductor package, a core substrate, a prepreg, a build-up material, or a solder resist.
<4> The method of measuring physical properties according to any one of <1> to <3>, wherein the preparation step includes measuring a mass of the member that has been moistened.
<5> The method of measuring physical properties according to any one of <1> to <4>, wherein:
  in the measurement step, at least a first deformation rate, which is a deformation rate of the member after heating and before cooling, and a second deformation rate, which is a deformation rate of the member after cooling, are measured using the digital image correlation method, and
  the method further comprises a deriving step of deriving a thermal expansion coefficient of the member in the heating and cooling step based on the first deformation rate and the second deformation rate.
<6> The method of measuring physical properties according to any one of <1> to <4>, wherein:
  a first mass is obtained by measuring a mass of the member during the heating and cooling step, and a third deformation rate which is a deformation rate of the member corresponding to the first mass is measured using a digital image correlation method, and
  the method further comprises a deriving step of deriving a thermal expansion coefficient of the member in the heating and cooling step based on the first mass and the third deformation rate.
<7> The method of measuring physical properties according to any one of <1> to <4>, wherein:
  the heating and cooling step and the measurement step are repeatedly performed, and a mass of the member and a deformation rate of the member are measured for each combination of the heating and cooling step and the measurement step when the heating and cooling step and the measurement step are repeatedly performed.

<8> The method of measuring physical properties according to <7>, wherein:
at least a first deformation rate, which is a deformation rate of the member after heating and before cooling, and a second deformation rate, which is a deformation rate of the member after cooling, are measured using the digital image correlation method for each combination of the heating and cooling step and the measurement step, and
the method further comprises a deriving step of deriving a thermal expansion coefficient of the member in each of the heating and cooling steps based on the first deformation rate and the second deformation rate.

<9> The method of measuring physical properties according to <7>, wherein:
a first mass is obtained by measuring a mass of the member during the heating and cooling step, and a third deformation rate, which is a deformation rate of the member corresponding to the first mass, is measured using a digital image correlation method for each combination of the heating and cooling step and the measurement step, and
the method further comprises a deriving step of deriving a thermal expansion coefficient of the member in each of the heating and cooling steps based on the first mass and the third deformation rate.

<10> A method of evaluating a member, comprising:
the method of measuring physical properties according to <5> or <8>; and
an evaluation step of deriving a water absorption rate of the member after the heating and cooling step corresponding to the second deformation rate, and evaluating a relationship between the derived water absorption rate, the thermal expansion coefficient, and a thermal expansion coefficient of a comparative member that contains the organic material and that has not been moistened.

<11> A method of evaluating a member, comprising:
the method of measuring physical properties according to <6> or <9>; and
an evaluation step of deriving a water absorption rate corresponding to the third deformation rate, and evaluating a relationship between the derived water absorption rate, the thermal expansion coefficient, and a thermal expansion coefficient of a comparative member that contains the organic material and that has not been moistened.

<12> A method of manufacturing an electronic component device, the method comprising:
selecting a material that is an organic material or a composite material including the organic material, on the basis of the method of evaluating a member according to <10> or <11>; and
manufacturing an electronic component device using the selected material.

<13> A method of manufacturing a material for an electronic component device, the method comprising:
selecting a material that is an organic material or a composite material including the organic material, on the basis of the method of evaluating a member according to <10> or <11>; and
manufacturing a material for an electronic component device using the selected material.

<14> A physical property measurement system, comprising:
a temperature control chamber including an arrangement portion in which a moistened member containing an organic material and having a known water absorption rate and a known mass is arranged, and a temperature control unit that heats and cools the member arranged in the arrangement portion;
a deformation rate measurement unit that measures a deformation rate of the member arranged in the arrangement portion using a digital image correlation method; and
a mass measurement unit that measures a mass of the member.

<15> The physical property measurement system according to <14>, wherein the mass measurement unit is arranged in the temperature control chamber and measures a mass of the member arranged in the arrangement portion.

Advantageous Effects of Invention

The disclosure can provide the method of measuring physical properties and the physical property measurement system capable of evaluating the relationship between the deformation rate and the water absorption rate of a member containing an organic material regardless of the correlation between the thermal deformation and the water absorption rate, and the method of evaluating a member, the method of manufacturing an electronic component device, and the method of manufacturing a material for an electronic component device including this method.

DESCRIPTION OF EMBODIMENTS

Figure 1:
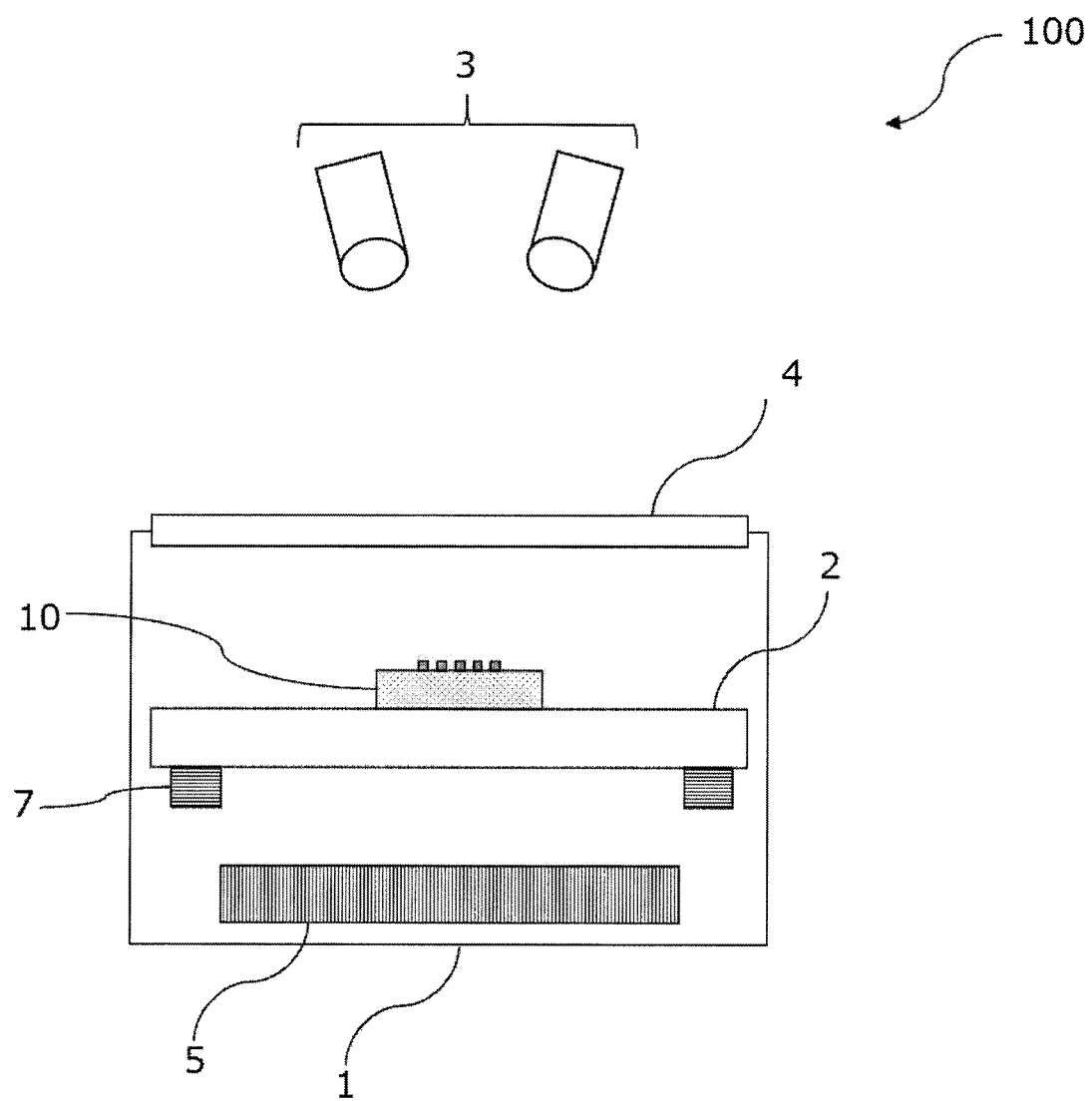
FIG. 1 is a cross-sectional view showing a schematic configuration showing an example of a physical property measurement system of the disclosure.

Hereinafter, embodiments for carrying out the present invention will be described in detail. However, the invention is not limited to the following embodiments. In the following embodiments, the components (including element steps and the like) are not essential unless otherwise specified. The same applies to numerical values and ranges thereof, and the invention is not limited thereto.

In the disclosure, a numerical range indicated using "to" includes numerical values described before and after "to" as a minimum value and a maximum value, respectively.

In the numerical ranges described in stages in the disclosure, the upper limit value or the lower limit value described in one numerical range may be replaced with the upper limit value or the lower limit value of the numerical range described in another stage. In addition, in the numerical range described in the disclosure, the upper limit value or the lower limit value of the numerical range may be replaced with a value shown in Examples.

In the disclosure, the term "layer" or "film" includes not only a case where the layer or film is formed in the entire region when a region where the layer or film exists is observed, but also a case where the layer or film is formed only in a part of the region.

In the disclosure, the term "stacked" refers to stacking layers, and two or more layers may be joined, or two or more layers may be detachable.

In the disclosure, the "water absorption rate" means the proportion of moisture contained in a specific member, and does not mean the performance (saturated water absorption rate) of how much moisture can be contained in a specific member.

[Method of Measuring Physical Properties]

A method of measuring physical properties of the disclosure includes: a preparation step of preparing a moistened member containing an organic material and having a known water absorption rate and a known mass; a heating and cooling step of performing heating and then cooling the member; and a measurement step of measuring a mass of the member at least one of during the heating and cooling step and after the heating and cooling step, and measuring a deformation rate of the member using a digital image correlation method.

In the method of measuring physical properties of the disclosure, the moistened member having a known water absorption rate and a known mass is prepared, and heating and cooling are performed using this member. In at least one of during the heating and cooling step and after the heating and cooling step, the mass of the member is measured, and the deformation rate of the member is measured using the digital image correlation method. By measuring the mass of the member, the water absorption rate of the member at the time of measurement can be obtained. As described above, data of the deformation rate and the water absorption rate of the member can be obtained. From the data of the deformation rate and the water absorption rate of the member, the relationship between the deformation rate and the water absorption rate of the member can be evaluated in both the case where there is a correlation between the thermal deformation and the water absorption rate and the case where there is no correlation between the thermal deformation and the water absorption rate.

Hereinafter, each step in the measurement method of the disclosure will be described.

(Preparation Step)

The method of measuring physical properties of the disclosure includes the preparation step of preparing a moistened member containing an organic material and having a known water absorption rate and a known mass.

For example, in the preparation step, a member containing an organic material may be prepared first. The member to be prepared first may be a member that has been moistened or may be a dried member.

The member used in the measurement method of the disclosure is not particularly limited as long as it contains an organic material, and may be a conventionally known electronic component, a measurement sample obtained from a member used for an electronic component, or the like. Examples of the member used in the measurement method of the disclosure include measurement samples obtained from a multilayer wiring board, a laminate, a semiconductor package, a core substrate, a prepreg, a build-up material, and a solder resist. Examples of the measurement sample include samples obtained by processing, cutting, or the like various members, samples obtained by removing a metal film such as a copper foil from various members, and the like.

The organic material contained in the member is not particularly limited, and examples thereof include conventionally known resins. The resin may be a thermoplastic resin, a thermosetting resin, or a photocurable resin.

Examples of the thermoplastic resin include polyethylene, polypropylene, polycarbonate, polystyrene, polyvinyl chloride, a vinyl-based polymer, polyester, polyamide, an acrylonitrile-butadiene-styrene copolymer resin (ABS resin), an acrylic resin, an acrylonitrile-ethylene-propylene-diene-styrene copolymer resin (AES resin), and a thermoplastic elastomer.

Examples of the thermosetting resin include a silicone resin, a urethane resin, a melamine resin, an epoxy resin, a phenol resin, and a urea resin.

Examples of the photocurable resin include an acrylic resin using radical polymerization and an epoxy resin using cationic polymerization.

In addition, the organic material may be a resin alone, or may be a mixture of a resin and another organic material, an inorganic material, or the like. Examples of the mixture include a resin composition containing a resin, an inorganic filler, and the like, and a material in which reinforcing fibers such as glass fibers and carbon fibers are impregnated with a thermosetting resin such as an epoxy resin.

The glass fiber may be in the form of a glass cloth such as a glass woven fabric, a glass nonwoven fabric, or a glass paper.

In the preparation step of the disclosure, a moistened member having a known water absorption rate and a known mass may be prepared through the following (1) to (4) in this order.

(1) A member containing an organic material is heated to dry the member.
(2) The mass of the dried member is measured.
(3) The member is caused to be moistened.
(4) The mass of the member after moisture absorption is measured.

In the above (1), moisture contained in the member is volatilized by heating to dry the member. The atmosphere and temperature for heating the member are not particularly limited as long as moisture contained in the member can be volatilized.

Examples of the heating atmosphere include a dry atmosphere substantially containing no moisture, and an inert gas atmosphere. For the purpose of easily volatilizing moisture, decompression from atmospheric pressure may be performed by a vacuum pump or the like.

The temperature at which the member is heated is not particularly limited as long as moisture contained in the member can be volatilized, and may be appropriately adjusted by, for example, a heating atmosphere, an air pressure at the time of heating, heat resistance of the organic material, and the like. The temperature at which the member is heated may be, for example, 100° ° C. to 150° C., or 110° ° C. to 130° C.

The time for heating the member may be, for example, 1 hour to 5 days, or 10 hours to 3 days.

The member obtained in the above (1) is a member from which moisture has been removed, and serves as a reference in obtaining the water absorption rate of the member described later. The water absorption rate of the member to be described later is a relative value when the water absorption rate of the member obtained in the above (1) is regarded as 0%. Therefore, the member obtained in the above (1) is not limited to a member from which moisture has been completely removed.

In the above (2), the mass of the dried member is measured. The temperature condition for measuring the mass is not particularly limited, and may be 15° C. to 30° C. or a room temperature (for example, 25° C.)

For the dried member, the surface thereof may be subjected to image analysis by a digital image correlation method, and a reference of measurement of the deformation rate of the member using the digital image correlation method performed later may be obtained. That is, the deformation rate of the member to be described later may be a deformation rate of the member based on the member dried in the above (1).

The digital image correlation method is also referred to as digital image correlation (DIC), and is a method of measuring a change in a deformation amount of a test object in a non-contact manner by analyzing images before and after deformation of the test object. As the test object, a pattern or the like may be formed on a surface thereof, and a change in a deformation amount of the test object may be measured by performing image analysis of a change in the pattern or the like. In the case of forming a pattern or the like, image analysis may be performed by DIC, and it is preferable to form a pattern or the like using a component having heat resistance. A pattern or the like may be formed on a member to be tested before the above (1).

For example, two digital cameras are arranged at different angles in the thickness direction of the test object so that the area surface of the test object enters the field of view, and the change in the deformation amount of the test object may be measured using the digital images obtained by the two digital cameras. As a result, it is possible to measure the change in the deformation amount in the width direction and the length direction, which are directions orthogonal to the thickness direction of the test object. DIC uses the principle that human right and left eyes grasp perspective by parallax as well as upper, lower, left, and right views. The deformation rate of the member described later may be, for example, a deformation rate in the width direction (also referred to as the x direction), a deformation rate in the length direction (also referred to as the y direction), or an average deformation rate in the width direction and the length direction.

As a method of obtaining the thermal expansion coefficient, a method of measuring a deformation amount of a test object by thermomechanical analysis (TMA) is common. For example, also in Non-Patent Document 2 described above, it is considered that the thermal expansion coefficient is obtained by TMA. When the change in the deformation amount of the test object is measured by TMA, it is necessary to bring a glass rod or the like into contact with the test object. When the thermal expansion coefficient of the test object is low, the influence of the dimensional change of the test object due to the contact of the glass rod or the like with the test object increases, and there is a problem that the thermal deformation and the deformation due to the variation in the water absorption rate cannot be accurately evaluated. On the other hand, in the method of measuring physical properties of the disclosure, the change in the deformation amount of the test object is measured in a non-contact manner by DIC. Therefore, the influence of deformation of the test object due to factors other than the thermal deformation and the variation in the water absorption rate can be reduced, and the thermal deformation and the deformation due to the variation in the water absorption rate can be accurately evaluated.

In the above (3), the dried member is caused to be moistened. Conditions for causing the member to be moistened are not particularly limited. For example, the dried member may be exposed to conditions of 30° C. to 130° C. and 60 to 85% RH (relative humidity) for about 1 hour to 300 hours to be moistened.

In the above (4), the mass of the member after moisture absorption is measured. As a result, the water absorption rate of the member after moisture absorption can be obtained based on the following Formula (a).

Water absorption rate (%) of member after moisture absorption=100×([mass of member after moisture absorption]−[mass of dried member])/[mass of dried member]    (a)

Through the above (1) to (4), the moisened member having a known water absorption rate and a known mass can be prepared. The known mass means the mass of the moistened member (that is, the sum of the dried member and the moisture contained in the member).

(Heating and Cooling Step)

The method of measuring physical properties of the disclosure includes the heating and cooling step of performing heating and then cooling on the moistened member having a known water absorption rate and a known mass.

By performing heating and cooling on the member, moisture contained in the member is removed by volatilization or the like, so that the water absorption rate of the member varies before and after the heating and cooling step. Specifically, the water absorption rate of the member is reduced by performing the heating and cooling step. The atmosphere in which the heating and cooling step is performed is not particularly limited, and may be an air atmosphere, a dry atmosphere substantially containing no moisture, an inert gas atmosphere, or the like.

By performing heating on the member, the member is expanded and deformed by heat. By performing cooling on the member after heating, the member contracts and deforms.

In the heating and cooling step, it is preferable that the member is heated and cooled within a range of −65° C. to 300° C. As an example, the member may be heated from room temperature (for example, 25° C.) to 85° ° C., heated to 85° C., and then cooled to room temperature (for example, 25° C.).

(Measurement Step)

The method of measuring physical properties of the disclosure includes the measurement step of measuring a mass of the member at least one of during the heating and cooling step and after the heating and cooling step, and measuring a deformation rate of the member using a digital image correlation method. In the preparation step described above, the mass of the moistened member may be measured, and the water absorption rate of the member after moisture absorption may be obtained from the mass of the member in a dry state and the mass of the moistened member.

When the deformation rate of the member is measured during the heating and cooling step, the deformation rate of the member at any time point in the heating and cooling step may be measured. For example, the deformation rate of the member may be continuously measured when heating and cooling are performed, or the deformation rate of the member at a specific time point when heating and cooling are performed may be measured.

The heating and cooling step and the measurement step described above may be repeatedly performed. The mass of the member and the deformation rate of the member may be measured for each combination of the heating and cooling step and the measurement step when the heating and cooling step and the measurement step are repeatedly performed. By repeatedly performing the heating and cooling step, the mass of the member continuously varies. Further, it is possible to measure the mass of the member and the deformation rate of the member which are varied by the measurement step. By repeatedly measuring the varied mass of the member and the varied deformation rate of the member, a change in the water absorption rate of the member and a change in the deformation rate of the member can be confirmed.

(Deriving Step)

The method of measuring physical properties of the disclosure may further include a deriving step of deriving a thermal expansion coefficient of the member in the heating and cooling step based on the deformation rate of the member measured in the measurement step described above. When the heating and cooling step and the measurement step described above are repeatedly performed, the thermal expansion coefficient of the member in each heating and cooling step may be derived in the deriving step.

For example, in the measurement step described above, at least a first deformation rate which is a deformation rate of the member after heating and before cooling and a second deformation rate which is a deformation rate of the member after cooling may be measured using a digital image correlation method, and in the deriving step, a thermal expansion coefficient of the member in the heating and cooling step may be derived based on the first deformation rate and the second deformation rate. When the heating and cooling step and the measurement step described above are repeatedly performed, the thermal expansion coefficient of the member may be derived for each heating and cooling step based on the first deformation rate and the second deformation rate.

In the deriving step, the average deformation rate of the member before and after the heating and cooling step may be calculated using the second deformation rate, and the thermal expansion coefficient of the member in the heating and cooling step may be calculated from the following Formula (1).

Thermal expansion coefficient (ppm/° C.) of member in heating and cooling step=([first deformation rate (ppm)]−[average deformation rate (ppm) of member before and after heating and cooling step])/([temperature (° C.) after heating and before cooling]−[temperature (° C.) after cooling])  Formula (1)

The average deformation rate of the member described above can be calculated from ([deformation rate (ppm) of member before heating and cooling step]+[second deformation rate (ppm)])÷2 using the deformation rate of the member before heating and cooling step and the second deformation rate.

The first deformation rate and the second deformation rate mean a deformation rate of a member after heating and before cooling with respect to a reference member and a deformation rate of a member after cooling with respect to a dimension of a reference member. The member dried in the above (1) may be used as a reference, or the member before the heating and cooling step may be used as a reference.

The thermal expansion coefficient of the member in the heating and cooling step may be obtained by measuring the mass of the member in the heating and cooling step. For example, a first mass may be obtained by measuring a mass of the member during the heating and cooling step, and a third deformation rate which is a deformation rate of the member corresponding to the first mass may be measured using a digital image correlation method, and a thermal expansion coefficient of the member in the heating and cooling step may be derived based on the first mass and the third deformation rate in the deriving step. When the heating and cooling step and the measurement step described above are repeatedly performed, the thermal expansion coefficient of the member may be derived for each heating and cooling step based on the first mass and the third deformation rate.

By measuring the mass of the member during the heating and cooling step, the thermal expansion coefficient, the water absorption rate, and the like can be calculated in real time for each temperature range during heating or cooling. For example, from the mass measurement result and the deformation rate measurement result during heating from 35° C. to 45° C., the water absorption rate and the thermal expansion coefficient in the vicinity of 40° ° C. can be calculated.

In the deriving step, a fourth deformation rate, which is a deformation rate caused by moisture absorption, excluding the influence of thermal expansion from the third deformation rate may be calculated and the thermal expansion coefficient of the member in the heating and cooling step may be calculated from the following Formula (2).

Thermal expansion coefficient (ppm/° C.) of member in heating and cooling step=([third deformation rate (ppm)]−[fourth deformation rate (ppm)])/([temperature at the time of measuring third deformation rate (° C.)]−[temperature at the start of heating and cooling step (C)])  Formula (2)

The fourth deformation rate can be obtained, for example, as follows. First, by using the water absorption rate of the member before the heating and cooling step, the mass of the member before the heating and cooling step, and the first mass, the water absorption rate of the member when the first mass is obtained is obtained. Furthermore, by using the deformation rate of the member before the heating and cooling step, the water absorption rate of the member before the heating and cooling step, and the water absorption rate of the member when the first mass is obtained based on the member dried in the above (1), the fourth deformation rate, which is the deformation rate caused by moisture absorption, excluding the influence of thermal expansion from the third deformation rate can be obtained.

[Evaluation Method 1 for Member]

The method 1 of evaluating a member of the disclosure includes: the method of measuring physical properties of the disclosure; and an evaluation step of deriving a water absorption rate of the member after the heating and cooling step corresponding to the second deformation rate, and evaluating a relationship between the derived water absorption rate, the thermal expansion coefficient of the member in the heating and cooling step, and a thermal expansion coefficient of a comparative member that contains the organic material and that has not been moistened.

In the evaluation method 1 of the disclosure, the influence of moisture absorption on the thermal expansion coefficient can be evaluated by comparing the thermal expansion coefficient of the member in the heating and cooling step with the thermal expansion coefficient of the comparative member that has not been moistened. For example, when the thermal expansion coefficient of the member in the heating and cooling step is decreased with respect to the thermal expansion coefficient of the comparative member that has not been moistened, it can be seen that the thermal expansion coefficient decreases due to moisture absorption, that is, there is a correlation between the thermal deformation and the water absorption rate. On the other hand, when the thermal expansion coefficient of the comparative member that has not been moistened and the thermal expansion coefficient of the member in the heating and cooling step are substantially the same, it can be seen that the thermal expansion coefficient does not substantially vary due to moisture absorption, that is, there is no correlation between the thermal deformation and the water absorption rate.

It is preferable that the comparative member that contains the organic material and that has not been moistened is a member after the member containing the organic material is heated and dried in the preparation step.

As a method of evaluating the relationship between the derived water absorption rate, the thermal expansion coefficient of the member in the heating and cooling step, and the thermal expansion coefficient of the comparative member, a graph may be created with one axis (for example, the x axis) as the thermal expansion coefficient and the other axis (for example, the y axis) as the water absorption rate. For example, (x, y)=(thermal expansion coefficient of member in heating and cooling step, water absorption rate of member after heating and cooling step) and (thermal expansion coefficient of comparative member, water absorption rate of comparative member) may be plotted. When the comparative member is a member after being dried as described above, the water absorption rate of the comparative member may be regarded as 0%.

In Evaluation Method 1 of the disclosure, when the heating and cooling step and the measurement step described above are repeatedly performed, the thermal expansion coefficient of the member in the n-th heating and cooling step and the water absorption rate of the member after the n-th heating and cooling step may be used (n is an integer of 1 or more). Furthermore, as the thermal expansion coefficient of the member in the n-th heating and cooling step and the water absorption rate of the member after the n-th heating and cooling step, two or more pieces of data of different n may be used.

[Evaluation Method 2 for Member]

The method 2 of evaluating a member of the disclosure includes: the method of measuring physical properties of the disclosure; and an evaluation step of deriving a water absorption rate corresponding to the third deformation rate, and evaluating a relationship between the derived water absorption rate, the thermal expansion coefficient of the member in the heating and cooling step, and a thermal expansion coefficient of a comparative member that contains the organic material and that has not been moistened.

Evaluation method 2 of the disclosure is different from Evaluation Method 1 of the disclosure described above in that the water absorption rate of the member during the heating and cooling step corresponding to the third deformation rate is used instead of the water absorption rate of the member after the heating and cooling step corresponding to the second deformation rate. Also in Evaluation Method 2 of the disclosure, the influence of moisture absorption on the thermal expansion coefficient can be evaluated by comparing the thermal expansion coefficient of the member in the heating and cooling step with the thermal expansion coefficient of the comparative member that has not been moistened.

In the evaluation method 2 of the disclosure, essential configurations, preferable configurations, and the like of the evaluation method 1 of the disclosure described above may be appropriately combined.

[Method of Manufacturing Electronic Component Device and Method of Manufacturing Material for Electronic Component Device]

A method of manufacturing an electronic component device or a method of manufacturing a material for an electronic component device of the disclosure is a manufacturing method of selecting an organic material on the basis of the evaluation method 1 of the disclosure or the evaluation method 2 of the disclosure described above, and manufacturing an electronic component device or a material for an electronic component device using the selected organic material.

When an organic material is selected based on Evaluation Method 1 of the disclosure or Evaluation Method 2 of the disclosure, an organic material having a correlation between the thermal deformation and the water absorption rate may be selected, or an organic material having no correlation between the thermal deformation and the water absorption rate may be selected.

Examples of the electronic component device include a multilayer wiring board and a semiconductor package. For example, a semiconductor package including an element and a cured product of a composition containing an organic material for sealing the element may be manufactured.

Examples of the material for an electronic component device include a laminate and a prepreg. For example, a laminate in which prepregs, which are sheets obtained by impregnating a base material such as paper or glass with a resin, are stacked may be manufactured, or copper foil may be applied to both surfaces of the laminate to form a copper-clad laminate.

[Physical Property Measurement System]

A physical property measurement system of the disclosure includes: a temperature control chamber including an arrangement portion in which a moistened member containing an organic material and having a known water absorption rate and a known mass is arranged, and a temperature control unit that heats and cools the member arranged in the arrangement portion; a deformation rate measurement unit that measures a deformation rate of the member arranged in the arrangement portion using a digital image correlation method; and a mass measurement unit that measures a mass of the member. By using the physical property measurement system of the disclosure, data of the deformation rate and the water absorption rate of the member can be obtained, and the relationship between the deformation rate and the water absorption rate of the member can be evaluated.

Hereinafter, an example of the physical property measurement system of the disclosure will be described with reference to FIG. 1. A physical property measurement system 100 includes a chamber 1 including a stage 2, a heater 5, a transfer plate 7, and a cooling supply unit (not shown), digital cameras 3 that acquire an image of a member 10 arranged on the stage 2, an analysis unit (not shown) that analyzes the image obtained by the digital cameras 3 to obtain a deformation rate of the member, and a mass measurement unit (not shown) that measures a mass of the member 10.

The stage 2 is arranged on the transfer plate 7 extending in the depth direction of the chamber 1. The member 10 containing an organic material is arranged on the stage 2 arranged in the chamber 1. The heater 5 is a heating unit for heating the member 10 in the heating and cooling step. The cold air supplying unit is a cooling unit for cooling the member 10 in the heating and cooling step.

The digital cameras 3 and the analysis unit are deformation rate measuring units that measure the deformation rate of the member 10 arranged on the stage 2 using a digital image correlation method. A transparent window 4 is provided in the upper part of the chamber 1.

A thermocouple may be arranged on the surface of the member 10 arranged on the stage 2 to measure the temperature of the member 10, particularly the temperature of the member 10 in the heating and cooling step. Alternatively, a member for temperature measurement having the same material or the like as the member 10 may be arranged so as to be adjacent to the member 10, and a thermocouple may be arranged on the surface of the member for temperature measurement. The temperature of the member for temperature measurement may be regarded as the temperature of the member 10.

The mass measurement unit may be arranged in the chamber 1 and measure the mass of the member 10 arranged on the stage 2. Alternatively, the mass measurement unit may be arranged outside the chamber 1 and measure the mass of the member 10 before and after the heating and cooling step. When the mass measurement unit is arranged in the chamber 1, the mass of the member can be measured during the heating and cooling step.

EXAMPLES

Hereinafter, the invention will be specifically described with reference to Examples, but the present invention is not limited to these Examples.

(Preparation of Core Substrate 1 after Drying)

A core substrate with copper foil (thickness: 0.7 mm) in which a copper foil was attached to a core substrate containing a resin cured product of an epoxy resin, an inorganic filler, and a glass cloth was cut into a size of 70 mm×60 mm using a shear to prepare three cut core substrates. Hereinafter, the same treatment was performed on the three cut core substrates to prepare three dried core substrates 1, and the subsequent treatments (Preparation of Core Substrate 1 after Drying) were also performed.

The cut end of the core substrate was polished with No. 4,000 sandpaper. Next, the cut core substrate was immersed in an aqueous solution of ammonium persulfate (manufactured by FUJIFILM Wako Pure Chemical Corporation) to remove the copper foil. Thereafter, the core substrate from which the copper foil had been removed was washed with pure water for 1 minute. The washed core substrate was dried by removing moisture with an air gun. White and black heat-resistant sprays were then applied to the core substrate. The heat-resistant sprays were applied thinly within a range that can be recognized by DIC. Thereafter, for the purpose of reproducibly measuring a region of 50 mm square, four corners of the core substrate were marked with a magic pen.

The core substrate was then placed in an oven and dried at 125° C. for 70 hours. The water absorption rate of the core substrate after drying was regarded as 0%.

The core substrate 1 after drying was prepared as described above.

(Moisture Absorption of Core Substrate 1)

Next, the mass of the core substrate 1 after drying was measured at 25° C. with an electronic balance.

After the mass measurement, the core substrate 1 (corresponding to the member 10 in FIG. 1) was arranged at the center of the glass stage 2 in the chamber 1 as shown in FIG. 1. The stage 2 was arranged on the metal transfer plate 7 extending in the depth direction of the chamber 1. Using the two digital cameras 3 arranged above the chamber 1 in the vertical direction, the image of the core substrate 1 was analyzed by DIC through the transparent window 4 provided in the upper part of the chamber 1. The position of the core substrate 1 at this time was used as a reference of the subsequent deformation rate of the core substrate 1.

After the measurement by DIC, the core substrate 1 was allowed to stand for 1 week under the conditions of 85° C. and 85% RH in the chamber 1 to cause the core substrate 1 to be moistened.

The mass of the core substrate 1 after moisture absorption was measured at 25° C. with an electronic balance. The water absorption rate of the core substrate 1 after moisture absorption was obtained from the mass of the core substrate 1 after drying and the mass of the core substrate 1 after moisture absorption.

(Heating and Cooling of Core Substrate 1 after Moisture Absorption, Etc.)

After the mass was measured, the core substrate 1 after moisture absorption was arranged at the center of the stage 2 in the chamber 1. The core substrate 1 was heated using the heater 5 arranged so as to face the core substrate 1 arranged on the stage 2. At this time, a core substrate (not shown) for temperature measurement having the same size and thickness as those of the core substrate 1 was arranged so as to be adjacent to the core substrate 1 in the depth direction of the chamber 1, a thermocouple (not shown) was arranged on the surface of the core substrate for temperature measurement, and the temperature of the thermocouple was regarded as the temperature of the core substrate 1. The core substrate 1 was heated from 25° C. to 85° C. After heating to 85° ° C., cold air was supplied into the chamber 1 to cool the core substrate 1 from 85° C. to 25° C. While the core substrate 1 was heated from 25° C. to 85° C. and cooled from 85° C. to 25° C., the image of the core substrate 1 was analyzed by DIC to obtain the deformation rate of the core substrate 1. For the deformation rate of the core substrate 1, the deformation rate in the width direction (x direction) and the deformation rate in the length direction (y direction) were obtained.

(Mass Measurement of Core Substrate 1 after Heating and Cooling, Etc.)

The mass of the core substrate 1 after heating and cooling was measured with an electronic balance at 25° C. Thereafter, each treatment described in (heating and cooling of the core substrate 1 after moisture absorption, etc.) and the mass measurement of the core substrate 1 after heating and cooling were repeatedly performed.

The water absorption rate of the core substrate 1 after the first heating and cooling was calculated from an average value of results of the mass measurement of the core substrate 1 before the first heating and cooling and after the first heating and cooling.

In the measurement by DIC during the first heating and cooling, the deformation rate of the core substrate 1 at 25° C. at the start of heating (corresponding to the deformation rate of the member before the heating and cooling step), the deformation rate of the core substrate 1 at 85° ° C. (corresponding to the first deformation rate), and the deformation rate of the core substrate 1 at 25° C. after the end of cooling (corresponding to the second deformation rate) were obtained.

The average deformation rate of the core substrate 1 during the first heating and cooling was obtained from [deformation rate (ppm) of member before heating and cooling step]+[second deformation rate (ppm)]/2. Using the average deformation rate of the core substrate 1 and the deformation rate of the core substrate 1 at 85° C., the thermal expansion coefficient of the core substrate 1 was calculated from Formula (1) described above. The average deformation rate was assumed to be a deformation rate caused by moisture absorption excluding the influence of thermal expansion at 85° C. By using the average deformation rate and the deformation rate of the core substrate 1 at 85° C., a thermal expansion coefficient calculated from deformation due to heat excluding deformation due to moisture absorption can be calculated.

Next, also in the second heating and cooling, the thermal expansion coefficient of the core substrate 1 was calculated in the same manner.

(Measurement of Physical Properties of Core Substrate 1 that had not been Moistened)

Three dried core substrates 1 were prepared in the same manner as described above (Preparation of Core Substrate 1 after Drying). The following treatments were performed on the three dried core substrates 1.

The mass of the core substrate 1 after drying was measured with an electronic balance at 25° C. Next, the dried core substrate 1 was arranged on the stage 2 in the chamber 1 in the same manner as described above without being caused to be moistened. Then, the core substrate 1 that had not been moistened was heated from 25° C. to 85° C. and cooled from 85° C. to 25° C. At this time, the deformation rate of the core substrate 1 at 85° C. was obtained by measurement using DIC, and the thermal expansion coefficient of the core substrate 1 that had not been moistened was calculated from the result.

The mass of the core substrate 1 that had not been moistened was measured after heating and cooling, and the water absorption rate of the core substrate 1 after heating and cooling was calculated.

Figure 2:
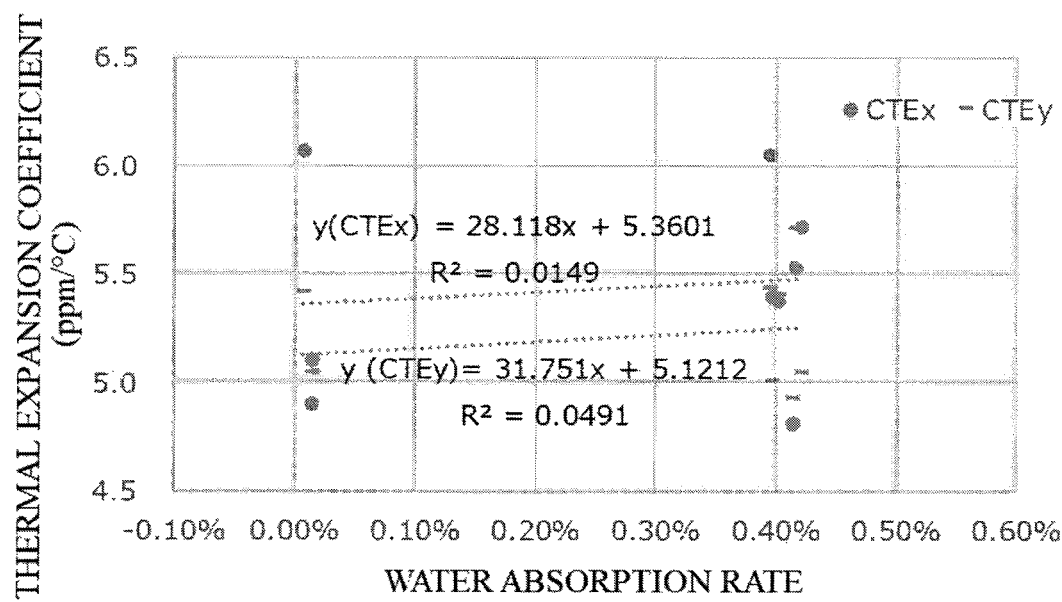
FIG. 2 is a graph showing a relationship between a water absorption rate and a thermal expansion coefficient of a core substrate 1.

FIG. 2 shows the results of the water absorption rate (data around 0.42%) of the core substrate 1 after moisture absorption and the thermal expansion coefficient of the core substrate 1 after the first heating and cooling, the water absorption rate (data around 0.40%) of the core substrate 1 after the first heating and cooling and the thermal expansion coefficient of the core substrate 1 after the second heating and cooling, and the water absorption rate (data around 0%) and the thermal expansion coefficient of the core substrate 1 that had not been moistened. In FIG. 2, CTEx means a value obtained based on the width direction (x direction), and CTEy means a value obtained based on the length direction (y direction).

In FIG. 2, there was no large difference between the thermal expansion coefficient of the core substrate 1 after heating and cooling and the thermal expansion coefficient of the core substrate 1 that had not been moistened. Therefore, it was confirmed that the thermal expansion coefficient of the organic material contained in the core substrate 1 did not greatly vary due to moisture absorption, and there was little dependency between the thermal deformation and the water absorption rate in the organic material.

(Preparation of Core Substrate 2 after Drying)

A core substrate with copper foil (thickness: 0.7 mm), which included a resin cured product of an epoxy resin different from the resin cured product of the epoxy resin included in the core substrate used in Experimental Example 1, and further included an inorganic filler and a glass cloth in which a copper foil was attached to the core substrate, was prepared, and a core substrate 2 after drying was prepared in the same procedure as in Experimental Example 1.

Figure 3:
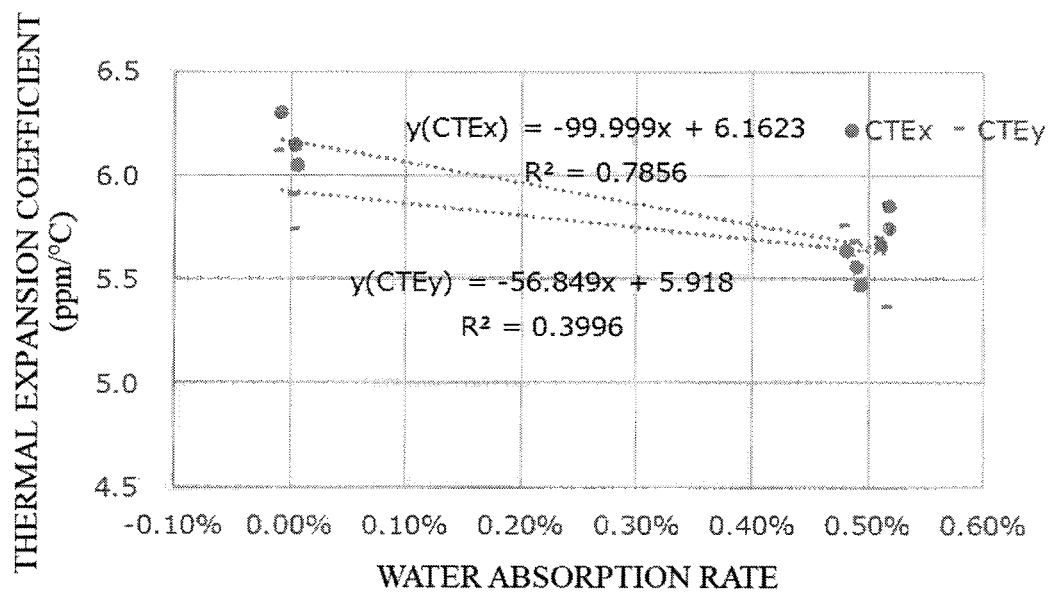
FIG. 3 is a graph showing a relationship between a water absorption rate and a thermal expansion coefficient of a core substrate 2.

Similarly to Experimental Example 1, the water absorption rate (data around 0.52%) of the core substrate 2 after moisture absorption and the thermal expansion coefficient of the core substrate 2 after the first heating and cooling, the water absorption rate (data around 0.48%) of the core substrate 2 after the first heating and cooling and the thermal expansion coefficient of the core substrate 2 after the second heating and cooling, and the water absorption rate (data around 0%) and the thermal expansion coefficient of the core substrate 2 that had not been moistened were obtained. These results are shown in FIG. 3. In FIG. 3, CTEx means a value obtained based on the width direction (x direction), and CTEy means a value obtained based on the length direction (y direction).

In FIG. 3, there was a large difference between the thermal expansion coefficient of the core substrate 1 after heating and cooling and the thermal expansion coefficient of the core substrate 2 that had not been moistened. Specifically, it was confirmed that the thermal expansion coefficient decreased as the water absorption rate increased. Therefore, it was confirmed that the thermal expansion coefficient of the organic material contained in the core substrate 2 decreased due to moisture absorption, and there was dependency between the thermal deformation and the water absorption rate in the organic material.

All documents, patent applications, and technical standards described in this specification are incorporated herein by reference to the same extent as if each document, patent application, and technical standard were specifically and individually indicated to be incorporated by reference.

The invention claimed is:

1. A method of measuring physical properties, the method comprising:
preparing a moistened member containing an organic material and having a known water absorption rate and a known mass;
heating and then cooling the member; and
measuring a mass of the member while heating and cooling the member, after heating and cooling the member, or any combination thereof; and measuring a deformation rate of the member using a digital image correlation method,
wherein the physical properties include the mass and deformation rate, the mass is used for obtaining a water absorption rate of the member at the time of measuring the mass, and the deformation rate is used for evaluating a relationship with the water absorption rate at the time of measuring the mass.

2. The method of measuring physical properties according to claim 1, wherein, in heating and cooling the member, the member is heated and cooled within a range of −65° C. to 300° C.

3. The method of measuring physical properties according to claim 1, wherein the member is a measurement sample obtained from a multilayer wiring board, a laminate, a semiconductor package, a core substrate, a prepreg, a build-up material, or a solder resist.

4. The method of measuring physical properties according to claim 1, wherein preparing the moistened member includes measuring a mass of the member that has been moistened.

5. The method of measuring physical properties according to claim 1, wherein:
in measuring the mass of the member, at least a first deformation rate, which is a deformation rate of the member after heating and before cooling, and a second deformation rate, which is a deformation rate of the member after cooling, are measured using the digital image correlation method, and
the method further comprises deriving a thermal expansion coefficient of the member in heating and cooling the member based on the first deformation rate and the second deformation rate.

6. The method of measuring physical properties according to claim 1, wherein:
a first mass is obtained by measuring a mass of the member during heating and cooling, and a deformation rate of the member corresponding to the first mass is measured using the digital image correlation method, and the method further comprises deriving a thermal expansion coefficient of the member in heating and cooling the member based on the first mass and the third deformation rate of the member corresponding to the first mass.

7. The method of measuring physical properties according to claim 1, wherein:

heating and cooling the member and measuring the mass of the member are repeatedly performed, and a mass of the member and a deformation rate of the member are measured for each combination of heating and cooling the member and measuring the mass of the member when heating and cooling the member and measuring the mass of the member are repeatedly performed.

8. The method of measuring physical properties according to claim 7, wherein:

at least a first deformation rate, which is a deformation rate of the member after heating and before cooling, and a second deformation rate, which is a deformation rate of the member after cooling, are measured using the digital image correlation method for each combination of heating and cooling the member and measuring the mass of the member, and the method further comprises deriving a thermal expansion coefficient of the member in each instance of heating and cooling the member based on the first deformation rate and the second deformation rate.

9. The method of measuring physical properties according to claim 7, wherein:

a first mass is obtained by measuring a mass of the member during heating and cooling, and a deformation rate of the member corresponding to the first mass, is measured using the digital image correlation method for each combination of heating and cooling the member and measuring the mass of the member, and the method further comprises deriving a thermal expansion coefficient of the member in each instance of heating and cooling the member based on the first mass and the third deformation rate of the member corresponding to the first mass.

10. A method of evaluating a member, comprising:

the method of measuring physical properties according to claim 5;

deriving a water absorption rate of the member after heating and cooling corresponding to the second deformation rate; and evaluating a relationship between the derived water absorption rate, the thermal expansion coefficient, and a thermal expansion coefficient of a comparative member that contains the organic material and that has not been moistened.

11. A method of evaluating a member, comprising:

the method of measuring physical properties according to claim 6;

deriving a water absorption rate corresponding to the deformation rate of the member corresponding to the first mass; and evaluating a relationship between the derived water absorption rate, the thermal expansion coefficient, and a thermal expansion coefficient of a comparative member that contains the organic material and that has not been moistened.

12. A method of manufacturing an electronic component device, the method comprising:

selecting a material that is an organic material or a composite material including the organic material based on the method of evaluating a member according to claim 10; and manufacturing an electronic component device using the selected material.

13. A method of manufacturing a mateiral for an electronic component device, the method comprising:

selecting a material that is an organic material or a composite material including the organic material based on the method of evaluating a member according to claim 10; and manufacturing a material for an electronic component device using the selected material.

14. A physical property measurement system, comprising:

a temperature control chamber including an arrangement portion in which a moistened member containing an organic material and having a known water absorption rate and a known mass is arranged, and a temperature control unit that heats and cools the member arranged in the arrangement portion;

a deformation rate measurement unit that measures a deformation rate of the member arranged in the arrangement portion using a digital image correlation method; and a mass measurement unit that measures a mass of the member, wherein the physical property includes the mass and deformation rate, the mass is used for obtaining a water absorption rate of the member at the time of measuring the mass, and the deformation rate is used for evaluating a relationship with the water absorption rate at the time of measuring the mass.

15. The physical property measurement system according to claim 14, wherein the mass measurement unit is arranged in the temperature control chamber and measures a mass of the member arranged in the arrangement portion.

16. The method of manufacturing a mateiral for an electronic component device, according 10 claim 13, wherein the mateiral for the electronic componennet a laminate or a prepeg.

17. A method of evaluating a member, comprising:

the method of measuring physical properties according to claim 8;

deriving a water absorption rate of the member after heating and cooling corresponding to the second deformation rate; and evaluating a relationship between the derived water absorption rate, the thermal expansion coefficient, and a thermal expansion coefficient of a comparative member that contains the organic material and that has not been moistened.

18. A method of evaluating a member, comprising:

the method of measuring physical properties according to claim 9;

deriving a water absorption rate corresponding to the deformation rate of the member corresponding to the first mass; and evaluating a relationship between the derived water absorption rate, the thermal expansion coefficient, and a thermal expansion coefficient of a comparative member that contains the organic material and that has not been moistened.

19. A method of manufacturing an electronic component device, the method comprising:

selecting a material that is an organic material or a composite material including the organic material based on the method of evaluating a member according to claim 10; and manufacturing an electronic component device using the selected material.

20. A method of manufacturing a mateiral for an electronic component device, the method comprising:

selecting a material that is an organic material or a composite material including the organic material based on the method of evaluating a member according to claim 10; and manufacturing a material for an electronic component device using the selected material.

\* \* \* \* \*